United States Patent [19]

Wong

[11] Patent Number: 4,849,355

[45] Date of Patent: Jul. 18, 1989

[54] METHOD OF TRANSFERRING GENES INTO CELLS

[76] Inventor: Tai-Kin Wong, SE. 375 Spokane St., Apt. C, Pullman, Wash. 99163

[21] Appl. No.: 142,320

[22] Filed: Dec. 30, 1987

Related U.S. Application Data

[63] Continuation of Ser. No. 689,657, Jan. 8, 1985, abandoned, which is a continuation-in-part of Ser. No. 315,944, Oct. 28, 1981, abandoned.

[51] Int. Cl.[4] ....................... C12P 21/00; C12P 19/34; C12N 15/00; C12N 7/00
[52] U.S. Cl. .................................... 435/172.3; 435/68; 435/91; 435/172.2; 435/173; 435/240.1; 435/243; 435/317.1; 435/320; 435/252.35; 536/27; 935/52
[58] Field of Search ............................. 47/1.5, 58, 61; 435/172.2, 172.3, 173, 68, 91, 240.1, 242, 253; 935/52, 72, 73, 75; 536/27

[56] References Cited

U.S. PATENT DOCUMENTS 4,292,408  9/1981  Zimmerman et al. .............. 435/173

OTHER PUBLICATIONS

Fromm et al. (1983) PNAS 82: 5824-8.
Zimmerman et al. (1981) Ag ewandte Chemie 20: 325-44.
Neumann et al. (1980) Neiturwissen haften 67: 414-415.

*Primary Examiner*—Thomas G. Wiseman
*Assistant Examiner*—Stephanie Seidman
*Attorney, Agent, or Firm*—Flehr, Hohbach, Test, Albritton & Herbert

[57] ABSTRACT

A method is provided for transferring genes into cells which comprises the step of subjecting the mixture of genes to be transferred and the target cells to an electric treatment.

10 Claims, 2 Drawing Sheets

METHOD OF TRANSFERRING GENES INTO CELLS

This is a continuation of Ser. No. 689,657 filed Jan. 8, 1985 now abandoned which is a continuation-in-part of Ser. No. 315,944 filed Oct. 28, 1981 now abandoned.

The present invention is a method to transfer genes to procaryotic or eucaryotic cells. In the fields of genetic engineering, cell biology, and embryo manipulation, various chemical and mechanical methods have been developed for transferring genetic materials into cells. Chemical methods involve the use of chemicals which permeabilize the cell surface, hence facilitates the transfer of the genetic materials into cells. [For reviews, see: Gerard Venema "Bacterial Transformation" in *Adv. Microbiol. Physl.* (1979) 19: 245–331; George Scangos and Frank H. Ruddle "Mechanisms and Applications of DNA-mediated Gene Transfer in Mammalian Cells - A Review" in *Gene* (1981) 14: 1–10; O. Wesley McBride and Jane L. Peterson "Chromosome-mediated Gene Transfer in Mammalian Cells" in *Ann. Rev. Genet.* (1980) 14: 321–345; Jürgen Horst et al., "On Procaryotic Gene Expression in Eucaryotic Systems" in *Human Genetics* (1980) 54: 289–302; R. Fraley and D. Papahadjopoulos, "New Generation Liposomes; The Engineering of an Efficient Vehicle for Intracellular Delivery of Nucleic Acids" in *Trends Biochem. Sci.* (1981) March. pp. 77–80.] Mechanical methods involve the injection of genetic materials directly into the cells, commonly known as microinjection (For review, see: W. French Anderson and Elaine G. Diacumakos "Genetic Engineering in Mammalian Cells" in *Scientific American* (1981) 245: 106–121).

In procaryotic systems, the chemical methods of transferring genes are usually employed, whereas in eucaryotic systems, both the chemical and mechanical methods are used.

All available methods, however, are somewhat dependent upon both the gene which is to be transferred and the recipient cells. Methods which may be used to transfer genes into procaryotes may not work in transferring genes into eucaryotes. However, according to the present invention, a single method is provided which may be utilized to transfer genes into either procaryotic or eucaryotic cells.

According to the present invention a solution, suspension or other mixture containing the gene to be transferred and the target cells are placed in a receptacle such that one electrode contacts the solution, suspension or mixture below the surface thereof. Preferably the said electrode is located at the lowest point of the said receptacle. Juxtaposed above the surface of the solution, suspension or mixture, but not in contact therewith is a second electrode directed towards the surface of the solution, suspension or mixture. The distance between the point of the second electrode and the surface of the solution, suspension or mixture is not critical. A distance of about 0.7 cm to about 4 cm has been used.

The electrodes may be connected to a conventional electric field generator. The electric field which may be applied to the solution or suspension containing the cells and gene must be high enough to create a high electric field or electric discharge but not great enough to substantially alter or destroy the cells or the gene. Voltages from approximately 3 kilovolts to 20 kilovolts may be used.

When an electric field is applied to the gene-cells mixture, the duration of the field varies from about 50 microseconds to 90 seconds depending on the nature of the target cells. When discharge condition is employed, a pulse discharge up to about 50 microseconds to 1 second is preferred. The number of pulses which may be applied to the solution, suspension or mixture containing the cells or gene may vary from about several pulses to about 300 pulses, depending upon the pulse width and intensity and the nature of the cells.

Figure 1:
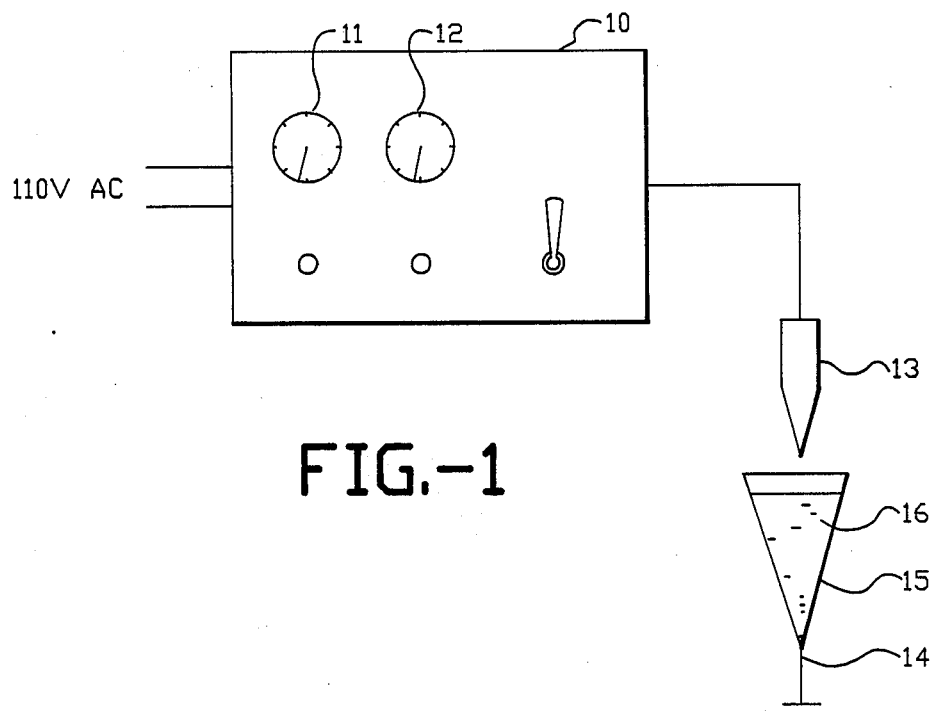
FIG. 1 is a diagram of an apparatus employed in the preferred embodiment of the invention.

Referring to FIG. 1, there is shown a conventional electric field generator 10 having a control and monitoring means 11 for applying field or pulse and an intensity control and measuring means 12 for voltage. Such a conventional generator is available, for example, from Andy Hish Associates, Van Nuys, Model Number ESD255 Electrostatic Discharge Generator with probe P255-1. Probe 13 is connected to said generator 10 and vertically disposed above vial receptacle 15. At the lowest point of vial receptacle 15 is located a ground electrode 14. Vial receptacle 15 contains a solution or suspension of cells and genes. As shown, vial receptacle 15 may be conical in shape and the ground electrode 14 is located at the apex thereof. Without limiting the invention to any particular theory, the shape of vial receptacle 15 may be preferred since there may be a concentration gradient of cells within the solution or suspension 16 due to the heterogeneity of the cells and in such case the gradient concentration of cells may be near the apex of vial receptacle 15. A preferred apparatus embodying the features of FIG. 1 is the BAEKON 2000, manufactured by Baekon, Inc., 20333 Merida Drive, Saratoga, California.

Figure 2:
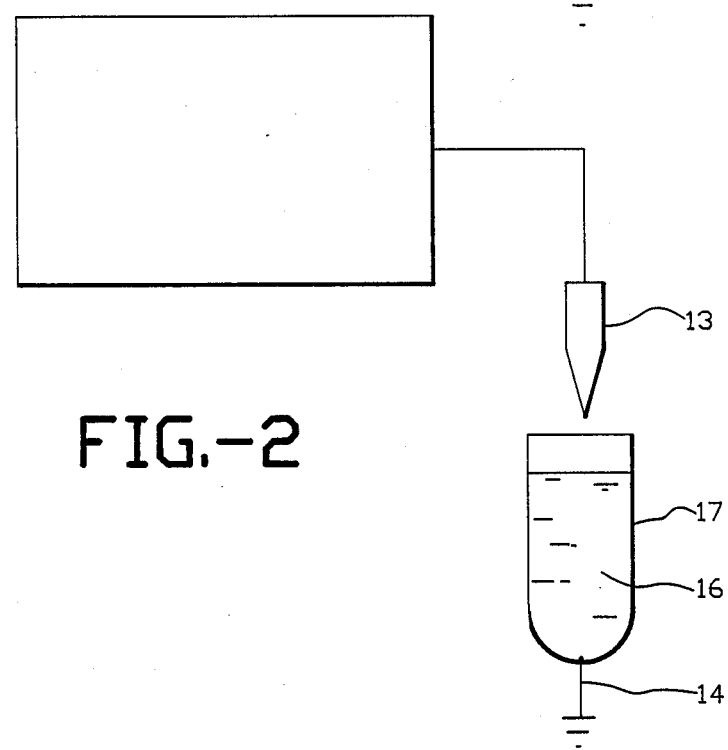
FIG. 2 is a diagram of an apparatus employed in a second embodiment of the invention.

Referring to FIG. 2 there is shown a second embodiment of the invention. FIG. 2 is similar to FIG. 1 except that receptacle 17 is a tube with a round bottom having the ground electrode located at the lowest point of the tube.

Figure 3:
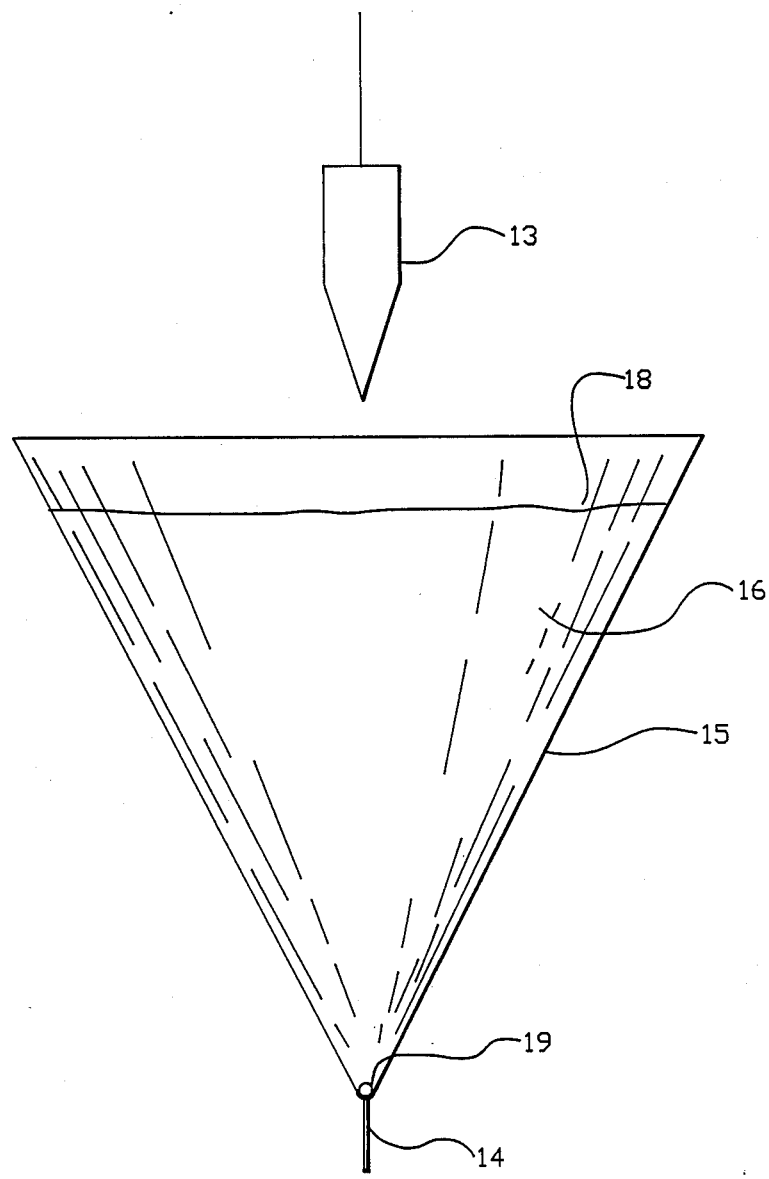
FIG. 3 is an enlarged view of a preferred receptacle shown in FIG. 1.

Referring to FIG. 3 there is shown an enlarged view of vial receptacle 15. As shown, a probe 13 is directed towards the surface 18 of the solution or suspension containing the cells and genes. Both the probe 13 and the vial 15 containing solution 16 may be exposed to the atmosphere during the experiment. It is readily apparent that the vial 15 need not be completely filled as shown in order to perform the experiment. A requirement is that the cells and gene containing solution or suspension is placed between direct discharge or electric field from probe 13 to ground electrode 14.

While not limiting the present invention to a particular theory, it is believed that by exposing the cells and genes to a high intensity electric field or electric discharge in the above described manner alters the cell surface sufficiently to allow the passage of the gene therethrough.

According to the present invention genes may be transferred to cells, including microorganisms, plant, animal and human cells. For example, Herpes simplex virus thymidine kinase gene may be transferred into mouse LM (TK−) cells.[1] Also the *E. coli* xanthine-guanine-phosphoribosyltransferase gene (Ecogpt)[2] alone or together with the Herpes simplex virus thymidine kinase gene may be transferred into human C10 (HGPRT−)[3] or C10 (HGPRT−TK−) cells, respectively. Even the bacterial mercury resistance gene which is in the plasmid pKT004 may be transferred into mouse LM (TK−) cells and renders the mouse cells mercury resistant. In all cases, cells which received the corresponding genes grow under conditions in which the parental cells do not survive.

According to the present invention genes may also be transferred into procaryotic cells. For example, various plasmids shown below in Table 1 may be transferred into E. coli of strains HB101,[5] RR1,[5] or M15[7].

TABLE 1

| PLASMIDS TRANSFERRED INTO E. coli CELLS | | |
|---|---|---|
| Plasmids | Genetic Marker(s) | |
| pBR322[5] | $Amp^{RX}$ | $Tet^R$ |
| pACYC184[6] | $Tet^R$, | $Cam^R$ |
| pACYC177[6] | $Amp^R$ | $Kan^R$ |
| pTW5[8] | $Lac^+$ | |
| pKT004[9] | $Hg^R$ | |
| pFG5[10] | $Amp^R$ | |

(X) Abbreviation: Amp: Ampicillin; Tet; Tetracycline; Cam: Chloramphenicol; Kan: Kanamycin; R: Resistance; Lac+: Lactose positive; Hg: Mercury According to the present invention virtually any gene may be transferred into virtually any target cell, as exemplified in, but not limited to, the following:

mercury resistance gene into plant cells (carrot, tomato, tobacco, barley, etc.)
plasmids/genes into yeast;
plasmids/genes into Streptomyces;
plasmids/genes into Bacillus;
plasmid Ti alone or together with other genes into plant cells;
plasmids/genes into human and animal cells, embryos, fertilized eggs or oocytes;
plasmids/genes into Pseudomonas; etc.

The genes which may be transferred according to the present invention may be structural genes, i.e., DNA fragments comprising the gene, or may be genes on vectors, such as, plasmid vectors, bacteriophage vectors, viral vectors or yeast vectors.

The present invention may be utilized to produce cell lines which produce, for example, monoclonal antibodies; commodity biochemicals (e.g., enzymes, perfume based volatile molecules from musk, hormones, gammainterferon, cell growth factors or mediators, ginseng, plant alkaloids, etc.); antibiotics, and pharmaceuticals; etc.

In plant systems, many kinds of plant cells are not culturable. According to the present invention, this problem may be overcome by transferring plant transforming gene(s), e.g., the Ti plasmid and its derivatives, into plant cells to convert them into culturable cells. Thus, commodity products/chemicals may be harvested from culturing plant cells.

For purposes of illustrating the present invention the following examples are provided. However, the scope of the invention is not intended to be limited thereto.

EXAMPLE 1 Gene Transfer in Eucaryotic System

The preparation of cells for gene transfer is described as follows. Mouse LM(TK−) cells were grown in 75 cm² cell culture flasks with RPMI 1640 medium [11] supplemented with 10% fetal calf serum at 37° C. in a humidified atmosphere containing 5% carbon dioxide to a cell number of around $1 \times 10^7$ cells. Cells were washed, trypsinized, pelleted by centrifugation, and then resuspended in phosphate buffered saline (PBS).[12]

A typical 150 μl gene-cells mixture consists of $5 \times 10^5$ to $6 \times 10^6$ cells, 1 μg or less plasmid pFG5 DNA, and 30 μg or less sheared calf thymus DNA as carrier. The whole mixture was pipetted into the receptacle and subjected to the electric field utilizing the apparatus as shown in FIG. 1. The applied voltage was between 3.0 kilovolts to 20 kilovolts. The number of discharges is 75 at the frequency of about 1 discharge per second. At the end of the discharge treatment, the gene-cells mixture was pipetted into cell culture flasks (75 cm²) each containing 10 ml of RPMI 1640 medium supplemented with 10% fetal calf serum. After 24 hours of incubation at 37° C., 10 ml medium containing 2×HAT[13] were added. After around one to two weeks of incubation, cells which received the plasmid pFG5 DNA survived as thymidine kinase positive clones. Those cells which did not receive the gene died.

When the DNA fragment (3.4 kilobases in size) harbouring the thymidine kinase gene in lieu of the whole plasmid pFG5 was used, thymidine kinase positive clones were also obtained. In addition, thymidine kinase positive clones were obtained when an electric field was used, in lieu of the said discharge.

EXAMPLE 2 Gene Transfer in Procaryotic System.

Bacteria E. coli strain HB101 were grown in 10 ml of Luria broth (10 g/l tryptone, 5 g/l yeast extract, 5 g/l NaCl) at 37° C. to a cell density of about $6 \times 10^8$ cells/ml. Between 10 to 50 ng of plasmid pBR322 DNA were mixed with 100 μl of the bacteria. Plasmid pBR322 harbors two selectable genes, namely, ampicillin and tetracycline resistance genes. The gene-cells mixture was subjected to electrical treatment utilizing the apparatus shown in FIG. 1 and as described in Example 1. Transformants were selected by plating bacteria-plasmid mixture onto agar plates [1.35% (w/v) Difco agar in Luria broth] supplemented with either ampicillin (30 μg/ml) or tetracycline (15 μg/ml). Agar plates were incubated at 37° C. for at least 14 hours. Both ampicillin and tetracycline resistance bacterial colonies were obtained.

Experience has shown that when an "old" bacterial culture, i.e., an overnight culture which was left at room temperature for at least 24 hours, was used for the experiment carried out as described above, transformants were also obtained.

Experience has shown also that when E. coli strain M15 was used as the recipient cells for the plasmid pTW5 DNA using the lactose positive colonies selection system[14], lactose positive colonies were obtained.

EXAMPLE 3 Gene transfer into mouse liver cells.

One million of 17 days old Balb/c fetal mouse liver cells in 100 μl of phosphate buffered saline containing 20 mM $MgCl_2$ were mixed with 5.4 μg of plasmid DNA, pH06N1 (See ref. 4) and transferred to the BAEKON receptacle for electric pulses treatment. The condition of the treatment was:

| Amplitude (A) | 10 kV |
|---|---|
| Pulse Duration (P) | 62.5 μSec |
| Number of Pulses (NP) | 32 |
| Burst Time (B) | 0.05 Sec |
| Number of Cycles (CY) | 50 |
| Distance between Discharge Point and | 8 mm |

Surface of the Solution -continued

After the treatment, cells were dilutes with 2 ml of RPMI 1640* medium and were transferred to a 96-well Costar plate, 0.2 ml/well, and incubated for two (2) days before selective medium <RPMI 1640 supplemented with 200 μg/ml of G418 (See ref. 4)> was added. Medium changes were carried out every 2–4 days. After 17 days of incubation in the selective medium, cell clones appeared.

* For 500 ml culture medium:
RPMI 1640 Medium was supplemented with:
10% (Final Concentration) of Heat-inactivated fetal calf serum,
1 mM MEM sodium pyruvate (Gibco Cat. No.: 320/1360),
5 ml of 200 mM L-glutamine,
5 ml of 100× MEM non-essential amino acids (Gibco Cat. No.: 320/1140),
5 ml of a mixture of 10,000 Units of Penicillin and 10 μg of Streptomycin (Gibco Cat. No.: 600/5140),
10 mM of Hepes Cell clones were also obtained in similar experiments using plasmid DNA, pH06T2 (See ref. 4).

The appearance of clones in selective medium indicates that transformed cell lines can be established by transferring oncogenes into primary cells by the electric pulses mediated gene transfer method.

[1] S. Kit, D. Dubbs, L. Piekarski, T. Hsu, Deletion of Thymidine Kinase Activity from L Cells Resistant to Bromodeoxyuridine, *Exptl. Cell Research* 31 (1963) pp. 291–312.

[2] R.C. Mulligan, P. Berg, Expression of a Bacterial Gene in Mammalian Cells, *Science*, 209 (1980), pp. 1422–1427.

[3] W. Berthold, C. Tan, Y. H. Tan, Purification and in vitro Labelling of Interferon From a Human Fibroblastoid Cell Line, *J. Biol. Chem.*, 253 (1978) pp. 5206–5212.

[4] D. A. Spandidos and N. M. Wilkie (1984): Malignant transformation of early passage rodent cells by a single mutated human oncogene. Nature Vol. 301, pp. 469–475.

[5] R. L. Rodriguez, R. Tait, J. Shine, F. Bolivar, H. Heyneker, M. Betlach, H. W. Boyer, Characterization of Tetracycline and Ampicillin Resistant Plasmid Cloning Vehicles, in Molecular Cloning of Recombinant DNA. Ed. by W.A. Scott and R. Werner. *Academic Press* (1977) pp. 73–84.

[6] A.C.Y. Chang, S. N. Cohen, Construction and Characterization of Amplifiable Multicopy DNA Cloning Vehicles Derived from the p15A Cryptic Plasmid, *J. Bact.*, 134 (1978) pp. 1141–1156.

[7] J. R. Beckwith, A Deletion Analysis of the Lac Operator Region in Escherichia coli, *J. Mol. Biol.*, 8 (1964) pp. 427–430.

[8] Tai-kin Wong, Attempts to Characterize the "Late-Template" Properties of T5 DNA after Infection of E. coli and Some Aspects on the Mechanism of Plasmid pSC101 Mediated Tetracycline Resistance, Ph.D. Dissertation, Ruprecht-Karl-Universitat Heidelberg, 1978. West Germany.

[9] K. N. Timmis, F. Cabello, S. N. Cohen, Cloning and Characterization of EcoRI and HindIII Restriction Endonuclease-generated Fragments of Antibiotic Resistance Plasmids R6-5 and R6, *Molec. Gen. Genet.* 162 (1978) pp. 121–137.

[10] F. Colbere-Garapin, S. Chousterman, F. Horodniceanu, P. Kourilsky, A.C. Garapin, Cloning of the Active Thymidine Kinase Gene of Herpes Simplex Virus Type 1 in Escherichia coli, *Proc. Natl. Acad. Sci. USA*, 76 (1979) pp. 3755–3759.

[11] Gibco, Grand Island Biological Company, Catalog No. 430–1800.

[12] Oxoid Limited, England, Code BR14a.

[13] RPMI 1640 Supplemented with Hypoxanthine 13.6 μg/ml; Aminopterin 0.176 μg/ml; thymidine 3.78 μg/ml, modified from E. H. Szybalska, W. Szybalski, Genetics of Human Cell Lines. IV. DNA-mediated Heritable Transformation of a Biochemical Trait, Proc. Natl. Acad. Sci. USA, 48: (1962) pp. 2026–2034.

[14] MacConkey Agar Supplemented with 20mM IPTG, (Isopropyl-α-D-thiogalactopyranoside) Difco. Catalog No. 0075-05, IPTG: Sigma I-5502.

What is claimed is:

1. A method of transferring DNA into mammalian or bacterial cells which comprises the step of subjecting a mixture of said DNA and said cells to electric pulses of an amplitude in the range of from about 3 to about 20 kilovolts.

2. The method according to claim 1 wherein the said electric pulses produce an electric discharge.

3. A method according to claim 1 wherein said mixture is a suspension containing said cells and said DNA.

4. A method according to claim 3 wherein said cells are procaryotic cells.

5. A method according to claim 3 wherein said cells are eucaryotic cells.

6. A method according to claim 3 wherein said cells are Streptomyces.

7. A method according to claim 3 wherien said DNA are transferred into said cells on plasmid vectors.

8. A method according to claim 3 wherein said DNA are transferred into said cells on bacteriophage vectors.

9. A method according to claim 3 wherein said DNA are transferred into said cells on viral vectors.

10. A method according to claim 3 wherein said DNA are transferred into said cells on yeast vectors.

* * * * *